US005807835A

United States Patent [19]

Animati et al.

[11] Patent Number: 5,807,835

[45] Date of Patent: Sep. 15, 1998

[54] 3'-DEAMINO-4'-DEOXY-4'-AMINO-8-FLUOROANTHRACYCLINES

[75] Inventors: Fabio Animati, Rome; Paolo Lombardi, Cesate; Federico Arcamone, Nerviano, all of Italy

[73] Assignee: A. Menarini Industrie Farmaceutiche Riunite S.r.l., Florence, Italy

[21] Appl. No.: 699,898

[22] Filed: May 14, 1991

[30] Foreign Application Priority Data

May 14, 1990 [IT] Italy .................................... 20300A90

[51] Int. Cl.[6] ........................... A61K 31/70; C07M 15/24

[52] U.S. Cl. ................................................ 514/34; 536/6.4

[58] Field of Search ................................ 536/6.4; 514/34

[56] References Cited

U.S. PATENT DOCUMENTS 4,987,126 1/1991 Bargiotti et al. ......................... 536/6.4

*Primary Examiner*—Elli Peselev

*Attorney, Agent, or Firm*—Hedman, Gibson, & Costigan, P.C.

[57] ABSTRACT

New 8-fluoroanthracycline derivatives of formula I possessing antitumoral properties are described, together with their preparation and pharmaceutical compositions containing them.

16 Claims, No Drawings

3'-DEAMINO-4'-DEOXY-4'-AMINO-8-FLUOROANTHRACYCLINES

FIELD OF THE INVENTION

This invention relates to glycosidic derivatives of 8-fluoroanthracycline of formula I:

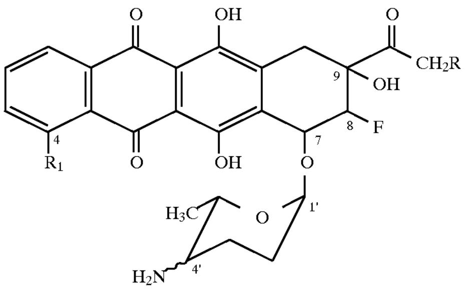

(I)

where:

R=H, OH, OR";

$R_1$=H, OH, $OCH_3$;

R"=CHO—$COCH_3$ or an acyl residue derived from a carboxylic acid containing up to 6 carbon atoms;

and ~$NH_2$ indicates that the amino substituent can be in the axial configuration (natural configuration) or equatorial configuration (epi configuration);

and their pharmaceutically acceptable salts.

STATE OF THE ART

Daunorubicin (daunomycin), 4-demethoxydaunorubicin (hydarubicin) and their derivatives comprising a hydroxylated side chain (doxorubicins) are glycosides possessing known antitumoral properties, the preparation and use of which have already been described (F. Arcamone "Doxorubicin Anticancer Antibiotics", Medicinal Chemistry Series Vol. 17. Academic Press, 1981).

It has now been surprisingly found that replacing an H atom with an F atom in the C-8 position of the non-glycosidic part of the molecule increases the activity and selectivity of these compounds, which thus unexpectedly possess superior power compared with known anthracyclines, especially in the case of tumoral cells resistant to known compounds.

DETAILED DESCRIPTION OF THE INVENTION

The present invention therefore relates to glycosidic derivatives of 8-fluoroanthracycline of formula (I):

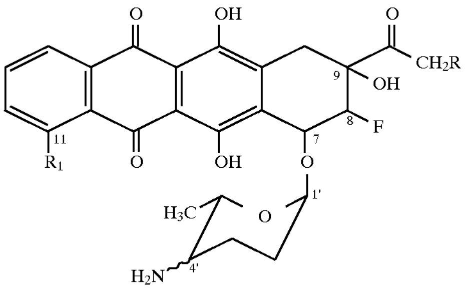

(I)

where:

R=H, OH, OR";

$R_1$=H, OH, $OCH_3$;

R"=CHO—$COCH_3$ or an acyl residue derived from a carboxylic acid containing up to 6 carbon atoms;

and ~$NH_2$ indicates that the amino substituent can be in the axial configuration (natural configuration) or equatorial configuration (epi configuration);

and their pharmaceutically acceptable salts.

One of the preferred salts of the present invention is the hydrochloride of compounds of formula (I).

More particularly the present invention relates to the following compounds:

4-demethoxy-8-fluoro-3'-deamino-4'-deoxy-4'-aminodaunorubicin (R=$R_1$=H);

4-demethoxy-8-fluoro-3'-deamino-4'-deoxy-4'-epi-aminodaunorubicin (R=$R_1$=H);

8-fluoro-3'-deamino-4'-deoxy-4'-epi-aminodaunorubicin (R=H, $R_1$=$OCH_3$);

8-fluoro-3'-deamino-4'-deoxy-4'-aminodaunorubicin (R=H, $R_1$=$OCH_3$);

8-fluoro-3'-deamino-4'-deoxy-4'-aminocarminomicin (R=H, $R_1$=OH);

8-fluoro-3'-deamino-4'-deoxy-4'-epi-aminocarminomicin (R=H, $R_1$=OH);

4-demethoxy-8-fluoro-3'-deamino-4'-deoxy-4'-aminodoxorubicin (R=OH, $R_1$=H); and its esters in C-14

4-demethoxy-8-fluoro-3'-deamino-4'-deoxy-4'-epi-aminodoxorubicin (R=OH, $R_1$=H); and its esters in C-14

8-fluoro-3'-deamino-4'-deoxy-4'-aminodoxorubicin (R=H, $R_1$=$OCH_3$); and its esters in C-14

8-fluoro-3'-deamino-4'-deoxy-4'-epi-aminodoxorubicin (R=H, $R_1$=$OCH_3$); and its esters in C-14

The compounds of formula (I) and their pharmaceutically acceptable salts are prepared by condensing an 8-fluoroanthracyclinone of formula (II):

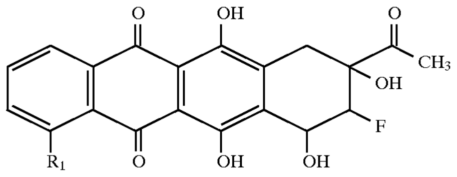

(II)

where $R_1$ is as heretofore defined, with a compound of formula IIIa or IIIe:

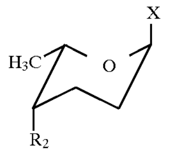

(IIIa)

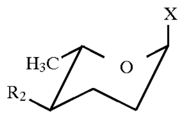

(IIIe)

in which X is a leaving group able to generate, under condensation conditions, a stable carbocation which can be attached by a hydroxyl group in position C-7, and $R_2$ is a protected amino group, to obtain the glycoside of formula (IV)

(IV)

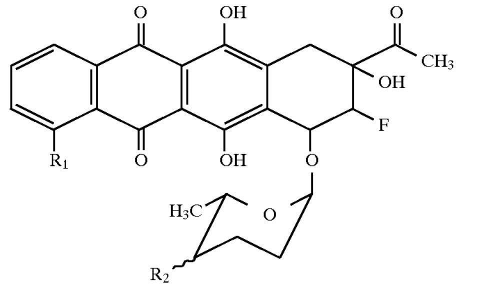

in which $R_1$ and $R_2$ are as heretofore defined and (~) indicates that the substituent $R_2$ can be arranged in the axial or equatorial configuration.

On removing the amino-protecting group from the compound of formula IV, the 8-fluoroanthracyclineglycoside of formula I is obtained in which R and $R_1$ are as heretofore defined.

The anthracyclineglycoside of formula I can be converted into one of its pharmaceutically acceptable salts, or alternatively the compound of formula I or a pharmaceutically acceptable salt can be brominated and the 14-bromo derivative obtained can be hydrolyzed to obtain the anthracyclineglycoside of formula I in which R=OH, and if desired said anthracyclineglycoside can be transformed into one of its pharmaceutically acceptable salts.

According to the present invention the preferred leaving group X for the compounds of formula III is a halogen such as bromine or chlorine, preferably chlorine, or a p-nitrobenzoyloxy group. An amino-protected $R_2$ group is preferably a trifluoroacetaside or an allyloxycarboxyamide.

The reaction conditions for the condensation reaction between a compound of formula II and one of formula IIIa or IIIe to obtain a compound of formula IV can vary according to the type of substitution of the compounds of formula IIIa or IIIe.

The glycosidation reaction is conducted in an inert organic solvent in the presence of a condensing agent.

Hydrocarbon solvents such as benzene or toluene, ethers such as diethyl-ether, tetrahydrofuran or dioxane, chlorinated solvents such as chloroform, methylenechloride or dichloroethane and their mixtures can be used. Methylenechloride is the preferred solvent.

Condensing agents can be salts such as silver triflate, silver perchlorate, mercury oxide and bromide mixtures, trimethylsilyltriflate; Lewis acids such as boron halides, tin or titanium tetrachloride; or acid ion exchange resins such as Amberlites.

The reaction temperature can vary from −40° C. to 40° C., preferably from −20° C. to 20° C., and the reaction can last from 15 minutes to 3 hours.

A dehydrating agent such as an activated molecular sieve is preferably present in the reaction mixture.

During the course of the reaction or at its end, an organic base such as pyridine, collidine, N,N-dimethylaminopyridine, triethylamine or proton sponge can be added to the reaction mixture.

According to the present invention the conditions for removing the amino-protecting group of the compound of formula IV in which $R_1$ and $R_2$ are as heretofore defined, in order to obtain a compound of formula I in which R=H and $R_1$ is as heretofore defined, can vary as a consequence of the mechanism of substitution of the compound of formula IV.

When the amino-protecting group is trifluoroacetamide, the deprotonation reaction is conducted in a polar solvent such as water, methanol, ethanol, pyridine, dimethylformamide or their mixtures in the presence of a stoichiometric or greater than stoichiometric quantity of an inorganic base such as NaOH, KOH, LiOH, $Ba(OH)_3$ or their carbonates. The reaction temperature can vary from 0° C. to 50° C. and the reaction can last from 3 hours to 3 days.

When the amino-protecting group is an allylcarboxyamide the deprotonation reaction is conducted in an inert solvent in the presence of a metal complex such as (tetrakistriphenylphosphine) palladium, as described for example in Tetrahedron Letters, 30, 3773 (1989), or (tetracarbonyl) nickel as described for example in J. Org. Chem. 38, 3233 (1973).

If necessary, a compound of formula I in which R is hydrogen and $R_1$ is as heretofore defined can be transformed, respectively, into a compound of formula I in which R is OH and $R_1$ is as heretofore defined, by bromination in position C-14 followed by hydrolysis of the 14-bromo derivative obtained in this manner. The bromination and subsequent hydrolysis are described in U.S. Pat. No. 4,122,076. The bromination of a compound of formula I in which R=H and $R_1$ is as heretofore defined is conducted with bromine in chloroform to obtain the corresponding 14-bromo derivative from which, after hydrolysis at ambient temperature for 48 hours with an aqueous sodium formate solution, a compound of formula I is obtained as a free base in which R=OH and $R_1$ is as heretofore defined, and which by treatment with hydrochloric acid in methyl alcohol is isolated as the hydrochloride.

The present invention also relates to the 8-fluoroanthracyclinones of general formula II and the process for their preparation.

This process is illustrated by the reaction scheme (A).

SCHEME A (V)

(VI)

(VII)

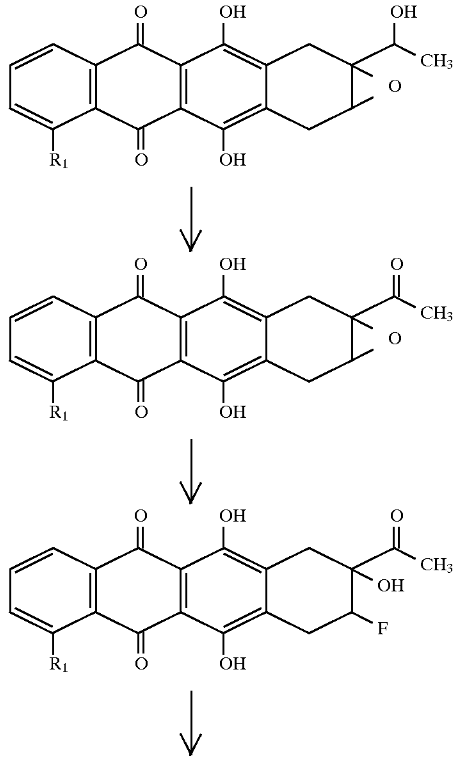

-continued

SCHEME A

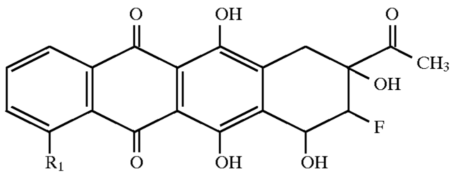

(II)

The first stage of the process comprises oxidizing an epoxyalcohol of general formula V in which $R_1$ is as heretofore defined, to obtain an epoxyketone of general formula VI in which $R_1$ is as heretofore described. The epoxyalcohol V can be prepared as described in GB-A-2 125 030. The oxidation reaction can be conducted by the methods generally known to the expert of the art. Methods comprising the use of dimethylsulphoxide, such as oxidation by the Moffat method and the like, or the use of pyridine-chromium complexes such as pyridinium chlorochromates, are preferred.

The second stage of the process illustrated in Scheme A comprises reacting the epoxyketone VI with a nucleophilic fluorine generator, to obtain the 8-fluorinated compound of general formula VII in which $R_1$ is as heretofore defined.

The nucleophilic fluorine generator can for example be the pyridine-hydrofluoric acid complex, and a preferred method for implementing this stage is to stir a solution or suspension of the compound of formula VI with the reagent at ambient temperature overnight. The last reaction stage comprises transforming the fluorohydro-ketone of formula VII into the compound of formula II. This can be done by known methods such as bromination and solvolysis, if necessary protecting the keto group [Can. J. Chem., 49, 2712 (1973); J. Am. Chem. Soc., 98, 1969 (1976); J. Am. Chem. Soc., 98, 1967 (1976)].

The present invention also relates to the amino sugars of formula III in which X and $R_2$ are as heretofore defined, and a process for their preparation comprising:

a) reacting methyl-2,3,6-trideoxy-α-L-glycero-hexoxypyranoside-4-ulose of formula VIII:

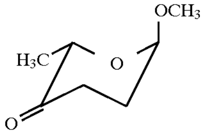

(VIII)

with a hydroxylamine or a salt of acid addition thereof to form a mixture of syn and anti oximes of formula IX:

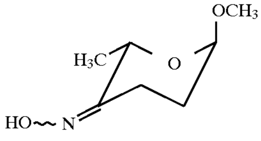

(IX)

b) reducing said mixture, after protecting the formed amino group with a trifluoroacetyl group and separating the 4-N-trifluoroacetylated epimers of formula Xa and Xe thus obtained:

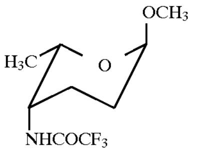

(Xa)

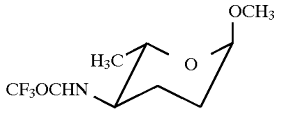

(Xe)

or, if preferred, protecting the formed amino group with an allyloxycarbonyl group and separating the 4-N-allyloxy-carbonylated pimers of formula XIa and XIe:

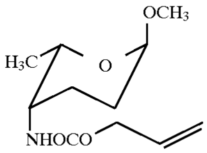

(XIa)

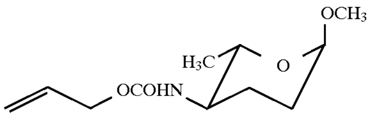

(XIe)

c) if preferred, as an alternative to the aforesaid stages, reacting the methyl-2,3,6-trideoxy-α-L-glycero-hexoxypyranoside-4-ulose of formula VIII with a reducing agent in the presence of ammonium salts, protecting the thus formed amino group with a trifluoroacetyl group or, if preferred, with an allyloxycarbonyl group, and separating the epimers of formula Xa and Xe or XIa and XIe;

d) converting each epimer Xa and Xe into the corresponding 1-hydroxy derivative of formula XIIa and XIIe:

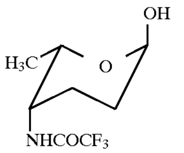

(XIIa)

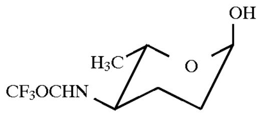

(XIIe)

or, if preferred, converting each epimer XIa and XIe into the corresponding 1-hydroxy derivative of formula XIIIa and XIIIe:

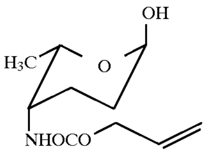

(XIIIa)

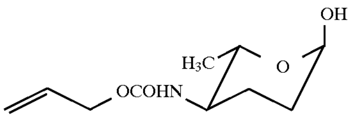

(XIIIe)

e) converting said 1-hydroxy derivatives XIIa and XIIe or XIIIa and XIIIe into the corresponding compounds of formula IIIa and IIIe, in which X is chlorine and $R_2$ is as heretofore defined, or, if desired, converting each said 1-hydroxy derivative XIIa and XIIe or XIIIa and XIIIe into the corresponding compounds of formula IIIa and IIIe, in which X is p-nitrobenzoyloxy and $R_2$ is as heretofore defined.

In stage a) the methyl-2,3,6-trideoxy-α-L-glycero-hexoxypyranoside-4-ulose VIII can be treated with hydroxylamine hydrochloride in triethylamine to give the syn and anti oximes IX.

In stage b) the oximes IX can be reduced with borane in tetrahydrofuran or bis-dimethoxyethoxy sodium aluminium hydride (Vitride) in tetrahydrofuran, toluene or dioxane. The reaction temperature can be between −20° C. and 20° C. and the reaction time between 3 and 12 hours. The reduced mixture can be reacted with trifluoroacetic anhydride in carbon tetrachloride or diethylether at ambient temperature, preferably in the presence of an organic base such as triethylamine or pyridine, to obtain a mixture of N-trifluoroacetylated derivatives from which the corresponding products of formula Xa and Xe are obtained separately by chromatographic separation. If preferred, the reduced mixture can be reacted with allylchlorocarbonate in tetrahydrofuran in the presence of an organic base such as pyridine, triethylamine or the like at a temperatre of between −20° C. and 20° C. for 3–12 hours, to obtain a mixture of N-allyloxycarbonylates from which the corresponding products of formula XIa and XIe are obtained by chromatographic separation.

Alternatively, in stage c), reduction of the ulose of formula VIII can be effected with sodium cyanoborohydride and ammonium acetate or ammonium chloride in tetrahydrofuran, diethylether, methanol or ethanol at a temperature of between −20° C. and 20° C. The reduced mixture can be treated as described in stage b).

In stage d) the conversion of each epimer Xa and Xe into the corresponding 1-hydroxy derivatives XIIa and XIIe or, if preferred, the conversion of each epimer XIa and XIe into the corresponding 1-hydroxy derivatives XIIIa and XIIIe can be effected by heating in the presence of an acid. Heating can be to a temperature of between 70° C. and 100° C. for a time of between 30 minutes and 3 hours, using an aqueous solution of acetic, trifluoroacetic or hydrochloric acid. The aqueous acid solution concentration can be between 5% and 30%.

In stage e) each 1-hydroxy epimer of formula XIIa, XIIe, XIIIa and XIIIe can be firstly treated overnight 0° C. with trifluoroacetic anhydride and then dissolved in diethyl ether and reacted overnight with gaseous hydrochloric acid to obtain each individual epimer of formula IIIa and IIIe in which X is chlorine and $R_2$ is a heretofore defined.

If preferred, each of said 1-hydroxy epimers of formula XIIa, XIIe, XIIIa and XIIIe can be dissolved in pyridine or dimethylformamide or dimethylsulphoxide in the presence of an organic base and treated with p-nitrobenzoylchloride at a temperature of between −20° C. and 20° C. for 1–6 hours to obtain each individual epimer of formula IIIa and IIIe in which X is n-nitrobenzoyloxy and $R_2$ is as heretofore defined.

The present invention also relates to pharmaceutical compositions containing as active principle an anthracyclineglycoside of formula I or a pharmaceutically active salt thereof together with a pharmaceutically acceptable carrier or diluent.

A therapeutically effective quantity of a compound according to the present invention is combined with an inert carrier. Conventional carriers can be used and the composition can be formulated in the usual manner.

The compounds according to the invention are effective in therapeutic treatment methods on man or animals for the conditions and at the doses used for doxorubicin as shown in the PDR (1987 Ed.), pp. 561–562 which is incorporated by reference. Doxorubicin (Adriamycin) has been used successfully to produce regression in disseminated neoplastic conditions such as acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma in which the small cell histologic type is the most responsive compared to other cell types and gastric carcinoma. In particular, the compounds of the invention are useful for the treatment of human cancer as antitumor agents, by administration of therapeutically effective quantities of the compound to the patient under treatment for leukemia, lymphomas, solid tumors and the like. The dose may be 1–300 $mg/m^2$, preferably 10–100 $mg/m^2$ daily given as a single dose or in divided doses IV every 1–3 weeks.

The following examples illustrate the invention but without in any way limiting its scope.

EXAMPLE 1

9-acetyl-9,8-(8H)-epoxy-7,10-dihydro-6,11-dihydroxy-5,12-naphthacene-dione (VI, $R_1$=H)

9-(1'hydroxyethyl)-9,8-(8H)-epoxy-7,10-dihydro-6,11-dihydroxy-5,12-naphthacene-dione (VI, $R_1$=H) prepared as described in GB-A-2 125 030 (1.9 g, 5.6 mmoles) dissolved in methylene chloride (150 ml) was added at ambient temperature under stirring to a suspension of pyridinium chlorochromate (1.8 g. 8.5 mmoles). The reaction mixture was kept stirring overnight, diluted by adding methylene chloride and washed with water (2×100 ml). The organic phase was dried over sodium sulphate, filtered and evaporated under vacuum to give a residue which was crystallized from ethyl acetate. 1.78 g (yield 90%) of the compound were obtained with a melting point of 219°–221° C.

I.R. (nujol, $cm^{-1}$): 1713

N.M.R. ($CDCl_3$, δ) 2.17 (s, 3H) 3.01 (dd. J=20 Hz, 1H) 3.4–4.2 (m, 4H) 7.80 (m, 2H) 8.30 (m, 2H) 13.39 (s, 1H) 13.42 (s, 1H)

Proceeding in like manner, the following were prepared:

4-methoxy-9-acetyl-9,8(8H)-epoxy-7,10-dihydro-6,11-dihydroxy-5,12-naphthacene-dione (VI, $R_1$=$OCH_3$) and 9-acetyl-9,8(8H) -epoxy-7,10-dihydro-4,6,11-trihydroxy-5,12-naphthacene-dione (VI, $R_1$=OH)

EXAMPLE 2

9-acetyl-8(8H)-fluoro-7,10-dihydro-6,9,11-trihydroxy-5,12-naphthacene-dione (VII, $R_1$=H)

A mixture of 9-acetyl-9,8(8H)-epoxy-7,10-dihydro-6,11-dihydroxy-5,12-naphthacene-dione (0.6 g, 1.7 mmoles), prepared as in Example 1, and hydrofluoric acid/pyridine (70% solution, 21 ml) was stirred or 24 hours in a nitrogen stream at ambient temperature. The reaction mixture was then poured into ice and water and stirred for 30 minutes. The precipitate obtained was filtered, washed with water until neutral and dried at 40° C. under vacuum. After crystallization 0.380 g (yield 60%) of the compound were obtained, with a melting point of 248°–252° C.

N.M.R. ($CDCl_3$, δ): 2.50 (d, 3H, $J_{hf}$=2.6 Hz) 3.0–3.4 (m, 4H) 4.25 (s, 1H) 4.78 (ddd, 1H, $J_{hf}$=48.4 Hz) 7.80 (m, 2H) 8.30 (m, 2H) 13.00 (s, 1H) 13.05 (s, 1H)

Proceeding in like manner, the following were prepared:

4-methoxy-9-acetyl-8(8H)-fluoro-7,10-dihydro-6,9,11-trihydroxy-5,12-naphthacene-dione (VII, $R_1$=$OCH_3$) and 9-acetyl-8(8H)-fluoro-7,10-dihydro-4,6,9,11-tetrahydroxy-5,12-naphthacene-dione (VII, $R_1$=OH)

EXAMPLE 3

9-acetyl-8(8H)-fluoro-10-hydro-6,7(7H),9,11-tetrahydroxy-5,12-naphthacene-dione (II, $R_1$=H)

A mixture of 9-acetyl-8(8H)-fluoro-7,10-dihydro-6,9,11-trihydroxy-5,12-naphthacene-dione (0.1 g, 0.26 mmoles), prepared as in Example 2, and bromine (0.4 mmoles) in carbon tetrachloride (30 ml) was irradiated for one hour with a 500 watt sun lamp. The reaction mixture was washed with a saturated aqueous sodium bicarbonate solution and then with water, dried over sodium sulphate, filtered and evaporated under vacuum to give a residue which was purified by flash chromatography. 0.028 g (yield 30%) of product were obtained.

N.M.R. ($CDCl_3$, δ): 2.54 (d, 3H, $J_{hf}$=2.2 Hz) 3.18 (dd, 1H, J=18 Hz) 3.30 (dd, 1H, J=18 Hz) 3.65 (d, 1H, $J_{hf}$=3 Hz) 4.60 (bs, 1H) 4.98 (dd, 1H, $J_{hf}$=46.2 Hz) 5.18 (bd, 1H, $J_{hf}$=13 Hz) 7.80–7.90 (m, 2H) 8.20–8.43 (m, 2H) 13.29 (s, 1H) 13.53 (s, 1H)

Proceeding in like manner, the following were prepared:

4-methoxy-9-acetyl-8(8H)-fluoro-10-hydro-6,7(7H),9,11-tetrahydroxy-5,12-naphthacene-dione (II, $R_1$=$OCH_3$) and 9-acetyl-8(8H)-fluoro-10-hydro-4,6,7(7H),9,11-pentahydroxy-5,12-naphthacene-dione (II, $R_1$=OH)

EXAMPLE 4

Methyl-2,3,4,6-tetradeoxy-4-trifluoroacetamido-α-L-threo-hexoxypyranoside (Xa) and methyl-2,3,4,6-tetradeoxy-4-trifluoroacetamido-α-L-erythro-hexoxypyranoside (Xe)

A mixture of 2.5 g of methyl-2,3,6-trideoxy-α-L-glycero-hexoxypyranoside-4-ulose (VIII), 2.4 g of hydroxylamine hydrochloride and 3.33 ml of methanol was kept under reflux for 2 hours. The solvent was evaporated under vacuum and the resultant oily residue was taken up in 150 ml of water and extracted with 200 ml of methylene chloride (3 times).

The extracts were dried over sodium sulphate, filtered, and evaporated under vacuum to give a residue which was purified by flash chromatography, eluting with 6/4 hexane/diethyl ether. 2.42 g of a syn/anti mixture of the oximes (IX) were obtained in viscous liquid form. This viscous liquid (0.830 g, 5.21 mmoles) was dissolved in toluene (15 ml), and bis methoxyethoxy sodium aluminium hydride (24.5 moles) was added dropwise at −40° C. to this solution under a nitrogen stream. The reaction mixture was kept stirring at −40° C. for ½ hour and at ambient temperature for 4 hours, after which water (0.5 ml), aqueous sodium hydroxide solution (0.5 ml) and water (1.5 ml, were added. The two phases were separated, the organic phase was dried over sodium sulphite, filtered through celite and evaporated under vacuum to give a crude compound which was suspended in carbon tetrachloride. Triethylamine (2.27 ml. 16.3 mmoles) and trifluoroacetic anhydride (1.15 ml, 6.24 moles) in carbon tetrachloride (10 ml) were added dropwise in that order to the suspension at 0° C. while stirring.

After 3 hours of further stirring at 0° C. the reaction mixture was diluted with methylene chloride and washed with water, with a 10% aqueous sodium bisulphate solution and with an 8% aqueous sodium bicarbonate solution. The organic phase was dried over sodium sulphate, filtered, and evaporated under vacuum to give a crude product which was purified by flash chromatography. Elution with 15/1 methylene/diethyl ether gave the compound Xa (0.480 g, yield 38%).

N.M.R. ($CDCl_3$, δ): 1.10 (d, 3H, J=8 Hz) 1.5–2.0 (m, 4H) 3.31 (s, 3H) 3.8–4.3 (m, 2H) 4.6–4.8 (m, 1H) 6.8 (s, 1H)

Elution with 10/1 methylene/diethyl ether gave the compound Xe 0.480 g, yield 38%).

N.M.R. ($CDCl_3$, δ): 1.15 (d, 3H, J=8 Hz) 1.7–1.9 (m, 4H) 3.32 (s, 3H) 3.6–3.8 (m, 2H) 4.6–4.7 (m, 1H) 6.8 (s, 1H)

EXAMPLE 5

Methyl-2,3,4,6-tetradeoxy-4-trifluoroacetamido-α-L-threo-hexoxypyranoside (Xa) and methyl-2,3,4,6-tetradeoxy-4-trifluoroacetamido-α-L-erythro-hexoxypyranoside (Xe)

A mixture of methyl-2,3,6-trideoxy-α-L-threo-hexoxypyranoside-4-ulose (VIII) (2 g, 13.8 moles), ammonium acetate (10.7 g, 139 mmoles) and sodium cyanoborohydride (2.84 g, 45 mmoles) in methanol (480 ml) was kept stirring at ambient temperature for 48 hours and then treated with a 5% aqueous acetic acid solution (240 ml). After 10 minutes of further stirring, the resultant solution was washed with chloroform (400 ml). The aqueous phase was separated, adjusted to pH 8 by adding sodium bicarbonate and extracted 7 times with 300 ml of chloroform.

The extracts were dried over sodium sulphite, filtered and evaporated under vacuum to give a crude product which after treatment with trifluoroacetic anhydride (5.8 ml) as described in Example 4. enables the two compounds Xa (0.28 g) and Xe (1.5 g) to be obtained.

EXAMPLE 6

Methyl-2,3,4,6-tetradeoxy-4-allyloxycarboxyamide-α-L-threo-hexoxypyranoside (XIa) and methyl-2,3,4,6-tetradeoxy-4-allyloxycarboxyamide-α-L-erythro-hexoxypyranoside (XIe)

The reduced mixture (0.58 g, 4 mmoles) obtained as described in Example 4 and dissolved in tetrahydrofuran (6 ml) was treated at 0° C. with pyridine (0.55 ml) and allylchlorocarbonate (0.82 g, 6.8 mmoles) dissolved in tetrahydrofuran (2 ml) in that order.

The reaction mixture was stirred for 6 hours at ambient temperature after which water was added and the mixture extracted with methylene chloride (5 times, each with 10 ml). The extracts were dried over sodium sulphate, filtered, and evaporated under vacuum to give a residue which was purified by flash chromatography. Elution with 9/1 petroleum ether/acetone gave successively the title compound XIa (0.366 g, yield 40%).

N.M.R. (200 MHz, $CDCl_3$, δ): 1.08 (d, J=65 Hz, 3H) 1.2–2.1 (s, 4H) 3.31 (s, 3H) 3.4–3.5 (m, 1H) 3.63 (d, 1H, J=10.73) 4.02 (td, 1H, $J_h$=6.5 Hz, $J_h$=1.6 Hz) 4.54 (d. 2H, J=5.6 Hz) 5.18 (dd, 1H) 5.27 (dd, 1H) 5.9 (m, 1H)

and the title compound XIe (0.395 g, yield 43%) NMR (200 MHz, $CDCl_3$, δ): 1.08 (d, J=6.5 Hz, 3H) 1.4–1.9 (m, 4H) 3.31 (s, 3H) 3.4–3.5 (m, 1H) 3.52 (qd, 1H, $J_{H\text{-}Me}$=6.5 Hz, $J_{H\text{-}H}$=9.9 Hz) 4.46 (d, 1H, J=10.7 Hz) 4.54 (d, 2H, J=5.6 Hz) 4.63 (d, 1H, J<1 Hz) 5.18 (dd, 1H) 5.27 (dd, 1H) 5.9 (m, 1H)

EXAMPLE 7

2,3,4,6-tetradeoxy-4-trifluoroacetamido-α-L-erythro-hexoxypyranosyl-p-nitrobenzoate (IIIe, $R_2$=$NHCOCF_3$, X=p-$NO_2$-$C_6H_4$—COO)

A mixture of 150 mg of methyl 2,3,4,6-tetradeoxy-4-trifluoro-acetamido-α-L-erythro-hexoxypyranoside (Xe), prepared as described in Example 5, and a 20% aqueous acetic acid solution (15 ml) was heated to 80° C. for 3 hours.

The reaction mixture was evaporated under vacuum to give 2,3,4,6-tetradeoxy-4-trifluoroacetamido-L-erythro-hexoxy-pyranoside (XIIe) in the form of a white solid which was dissolved in 2.5 ml of pyridine and treated at 0° C. with 177 mg of p-nitrobenzoylchloride. The reaction mixture was stirred for 2 hours at 0° C., water was added and the mixture extracted with chloroform (5 times, each with 3 ml). The extracts were washed with 3N sulphuric acid, water and an 8% aqueous sodium bicarbonate solution. The organic phase was dried over sodium sulphate, filtered and evaporated under vacuum to obtain the compound IIIe (200 mg, yield 85%) in the form of a viscous yellow liquid.

N.M.R. (60 MHz $CDCl_3$, δ): 1.25 (d, J=6 Hz, 3H) 1.9–2.2 (m, 4H) 3.6–4.0 (m, 2H) 6.0 (s, 1H) 6.35 (s, 1H) 8.2 (s, 4H)

EXAMPLE 8

2,3,4,6-tetradeoxy-4-trifluoroacetamido-α-L-threo-hexoxypyranosyl-p-nitrobenzoate (IIIa, $R_2$=$NHCOCF_3$, X=p-$NO_2$—$C_6H_4$—COO)

Starting from methyl-2,3,4,6-tetradeoxy-4-trifluoroacetamido-α-L-threo-hexoxypyranoside (Xa), prepared as described in Example 4, the said compound was prepared by the procedure described in Example 7.

TLC on Kieselgel plates (Merck $F_{254}$) using the solvent system: hexane/ethylacetate (3:1) $R_f$=0.43.

EXAMPLE 9

2,3,4,6-tetradeoxy-4-allyloxycarboxyamido-α-L-threo-hexoxypyranosyl-p-nitrobenzoate (IIIa, $R_2$=$NHCOOCH_2CH{=}CH_2$, X=p-$NO_2$—$C_6H_4$—COO)

A mixture of 200 mg of methyl-2,3,4,6-tetradeoxy-4-allyloxycarboxyamide-α-L-threo-hexoxypyranoside (XIa), prepared as described in Example 6, and 20 ml of 20% aqueous acetic acid solution was heated to 80° C. for 2 hours. The reaction mixture was evaporated under vacuum to give 2,3,4,6-tetradeoxy-4-allyloxycarboxyamido-α-L-threo-hexoxypyranose (XIIIa) in the form of a viscous liquid which was dissolved in 4 ml of pyridine and treated with 120 mg of p-nitrobenzoylchloride. The reaction mixture was stirred for 2 hours at 0° C., water was added and the mixture extracted with chloroform (5 times, each with 4 ml). The extracts were washed with 3N sulphuric acid, water and an 8% aqueous sodium bicarbonate solution. The organic phase was dried over sodium sulphate and evaporated under vacuum to obtain the compound IIIa (260 mg, yield 81%).

TLC on Kieselgel plates (Merck $F_{254}$) using the solvent system: dichloromethane/acetone (95:5) $R_f$=0.40.

EXAMPLE 10

2,3,4,6-tetradeoxy-4-allyloxycarboxyamido-α-L-erythro-hexoxypyranosyl-p-nitrobenzoate (IIIe, $R_2$=$NHCOOCH_2CH{=}CH$, X=p-$NO_2$—$C_6H_4$—COO)

Starting from methyl-2,3,4,6-tetradeoxy-4-allyloxy-carboxyamide-α-L-erythro-hexoxypyranoside (XIe), prepared as described in Example 6, the said compound was obtained by the procedure described in Example 9.

TLC on Kieselgel plates (Merck $F_{254}$) using the solvent system: hexane/ethylacetate (95:5) $R_f$=0.31.

EXAMPLE 11

2,3,4,6-tetradeoxy-4-trifluoroacetamido-α-L-erythro-hexoxypyranosylchloride (IIIe, $R_2$=NHCOCF, X=Cl A solution of 210 mg of 2,3,4,6-tetradeoxy-4-trifluoroacetaxido-α-L-erythro-hexoxy-pyranosyl-p-nitrobenzoate (IIIe, $R_2$=$NHCOCF_3$, X=p-$NO_2$—$C_6H_4$—COO), prepared in accordance with Example 7, in 5 ml of anhydrous methylene dichloride, was saturated at 0° C. with anhydrous hydrochloric acid. After standing overnight at 0° C. the precipitated p-nitrobenzoic acid was filtered off and the solution evaporated under vacuum to give the compound, which was used for the coupling reaction without further purification.

EXAMPLE 12

2,3,4,6-tetradeoxy-4-trifluoroacetamido-α-L-threo-hexoxy-pyranosylchloride (IIIa, $R_2$=$NHCOCF_3$, X=Cl Starting from 2,3,4,6-tetradeoxy-4-trifluoroacetamido-L-threo-hexoxy-pyranosyl-p-nitrobenzoate (IIIa, $R_2$=$NHCOCF_3$, X=P-$NO_2$—$C_6H_4$—COO), prepared as described in Example 8, the said compound was prepared following the procedure described in Example 11.

EXAMPLE 13

2,3,4,6-tetradeoxy-4-allyloxycarboxyamido-L-threo-hexoxy-pyranosylchloride (IIIa, $R_2$=$NHCOOCH_2CH_2CH_2$, X=Cl A solution of 270 mg of 2,3,4,6-tetradeoxy-4-allyloxycarboxyamido-L-threo-hexoxypyranosyl-p-nitrobenzoate (IIIa, $R_2$=$NHCOOCH_2CH_2CH_2$, X=p-$NO_2$—$C_6H_4$—COO), prepared in accordance with Example 9, in 6 ml of anhydrous methylene dichloride, was saturated with anhydrous hydrochloric acid. After standing overnight at 0° C. the precipitated p-nitrobenzoic acid was filtered off and the solution evaporated under vacuum to give the compound, which was used for the coupling reaction without further purification.

EXAMPLE 14

2,3,4,6-tetradeoxy-4-allyloxycarboxyamido-L-erythro-hexoxypyranosylchloride (IIIe, $R_2$=$NHCOOCH_2CH{=}CH_2$, X=Cl Starting from 2,3,4,6-tetradeoxy-4-allyloxycarboxymido-L-erythro-hexoxypyranosyl-p-nitrobenzoate (IIIe, $R_2$=$NHCOOCH_2CH{=}CH_2$, X=p-$NO_2$—$C_6H_4$—COO), prepared in accordance with Example 10, the said compound was obtained following the procedure described in Example 13.

EXAMPLE 15

4-demethoxy-8-fluoro-3'-deamino-4'-deoxy-4'epi-aminodaunorubicin hydrochloride (I, R=H, $R_1$=H)

A mixture of 120 mg of 9-acetyl-8(8H)-fluoro-10-hydro-6,7(7H),9,11 tetrahydroxy-5,12-naphthacenedione (II, $R_1$=H), prepared as described in EXAMPLE 3, 240 mg of 2,3,4,6-tetradeoxy-4-trifluoro-acetamido-α-L-erythro-hexopyranosyl-p-nitrobenzoate (IIIe, $R_2$=$NHCOCF_3$, X=p-$NO_2$—$C_6H_4$—COO), prepared as described in EXAMPLE 7, in 60 ml of dry methylene dichloride and 20 ml of diethyl ether and in the presence of molecular sieves (4 Å) at 0° C. was treated with 0.225 ml of trimethylsilyltriflate.

The reaction mixture was stirred during 15 minutes at 0° C. and quenched with 266 mg of 1,8-bis-(dimethylamino)-naphthalin, after stirring for 10 minutes. The mixture was filtered to remove the resulting white precipitate and the filtrate evaporated under vacuum to obtain a residue which was purified by flash chromatography.

Elution with ethylene/acetone (95:5) afforded 4-demethoxy-8-fluoro-3'-deamino-4'-deoxy-4'-epi-trifluoroacetamidodaunorubicin (IV, $R_1$=H, $R_2$=$NHCOCF_3$) (108 mg, yield 60%)

H-NMR (200 MHz, $CDCl_3$, δ): 1.15 (d, J=8 Hz, 3H) 1.7–1.9 (m, 4H) 2,45 (s, 3H) 3.19 (d, J=19 Hz, 1H) 3.33 (dd, $J_{H-F}$=3.6, J=19 Hz, 1H) 3.6–3.8 (m, 2H) 3.98 (s, 1H) 4.91 (dd, $J_{H-F}$=50 Hz, 1H) 5.17 (dd, $J_{H-F}$=12 Hz, 1H) 5.26 (m, 1H) 6.21 (bd, 1H) 7.86 (m, 2H) 8.4 (m, 2H) 13.35 (s, 1H) 13.36 (s, 1H)

A suspension of 78 mg of the N-trifluoroacetyl derivative in 15.6 ml of barium hydroxide 0.2M was stirred during 2 hours under nitrogen at room temperature. The reaction mixture was neutralized with carbon dioxide and then extracted with chloroform; the combined extracts were dried over anhydrous sodium sulphate and concentrated to a small volume. Hydrogen chloride and diethylether was added to give the title compound (I, R=H, $R_1$=H) (56 mg, yield 80%).

TLC on Kieselgel plates (Merck $F_{254}$) using the solvent system: chloroform/methanol/water (65:30:10) $R_f$=0.45.

By proceeding analogously the following compounds can be prepared 4-demethoxy-8-fluoro-3'deamino-4'-deoxy-4'-aminodaunorubicin hydrochloride (I, R=H, $R_1$=H)

TLC on Kieselgel plates (Merck $F_{254}$) using the solvent system: chloroform/methanol/water (65:30:10) $R_f$=0.47

H-NMR of the corresponding trifluoroacetamido derivative is reported

H-NMR (200 MHz, $CDCl_3$ inter alia δ): 3.17 (d, J=19 Hz, 1H, H-10 ax) 3.31 (dd, $J_{H-F}$=3.6, J=19 Hz, 1H, H-10 e); 3.8–4.3 (m, 2H, H-4', H-5'); 4.89 (dd, $J_{H-F}$=50 Hz, 1H, H-8) 5.25 (dd, $J_{H-F}$=12 Hz, 1H, H-7) 5.46 (m, 1H, H-1')

8-Fluoro-3'-deamino-4'-deoxy-4'-epi-aminodaunorubicin hydrochloride (I, R=H, $R_1$=$OCH_3$)

TLC on Kieselgel plates (Merck $F_{254}$) using the solvent system chloroform/methanol/water (65:30:10) $R_f$=0.41

H- NMR of the corresponding trifluoroacetamido derivative is reported:

H-NMR (200 MHz, $CDCl_3$, inter alia δ): 3.17 (d, J=19 Hz, H-10 ax); 3.5 (dd, $J_{H-F}$=3.6 Hz, J=19 Hz, 1H, H-10 e); 4.10 (s, 3H, $OCH_3$)

8-Fluoro-3'-deamino-4'-deoxy-4'-aminodaunorubicin hydrochloride (I, R=H, $R_1$=$OCH_3$)

TLC on Kieselgel plates (Merck $F_{254}$) using the solvent system chloroform/methanol/water (65:30:10) $R_f$=0.42

H- NMR of the corresponding trifluoroacetamido derivative is reported:

H-NMR (200 MHz, $CDCl_3$, inter alia δ): 3.15 (d, J=19 Hz, 1H, H-10 ax); 3.49 (dd, $J_{H-F}$=3.6 Hz, J=19 Hz, 1H, H-10 e); 4.08 (s, 3H, $OCH_3$)

EXAMPLE 16

4-demethoxy-8-fluoro-3'-deamino-4'-deoxy-4'-aminodaunorubicin hydrochloride (I, R=H, $R_1$=H)

A mixture of 200 mg of 9-acetyl-8(8H)-fluoro-10-hydro-6,7(7H),9,11-tetrahydroxy-5,12-naphthacenedione (II, $R_1$=H) prepared as described in EXAMPLE 3, 157 mg of 2,3,4,6 tetradeoxy-4-allyloxycarboxyamido-L-threo-hexopyranosylchloride (IIIa, R=$NHCOOCH_2$—CH═CH, X=Cl) prepared as described in EXAMPLE 13 in 60 ml of dry methylene dichloride and in the presence of molecular sieves (4 Å) at 0° C. was treated with a solution of 134 mg of silver trifluoromethanesulphonate in 10 ml of diethylether. After 45 minutes the mixture was filtered to remove the resulting white precipitate and the filtered solution was treated with a satured aqueous solution of sodium hydrogen carbonate. The organic layer was separated off and evaporated under vacuum to obtain a residue which was purified by flash chromatography.

Elution with methylene dichloride/acetone (95:5) afforded 4-demethoxy-8-fluoro-3'-deamino-4'-deoxy-4'-allyloxycarboxyamido (IV, $R_1$=H, $R_2$=$NHCOOCH_2CH$═$CH_2$) (160 mg, yield 53%)

H-NMR (200 MHz, $CDCl_3$, δ): 1.08 (d, J=6.5 Hz, 3H) 1.2–2.1 (m, 4H) 2.45 (s, 3H) 3.18 (dd, J=19 Hz, 1H) 3.31 (dd, $J_{H-F}$=3,6 Hz, J=19 Hz, 1H) 3.63 (bd, 1H) 3.38–3.52 (m, 1H) 4.02 (m, 1H) 4.54 (d,2H) 4.89 (dd, $J_{H-F}$=50 Hz, 1H) 5.15 (dd, $J_{H-F}$=12 Hz, 1H) 5.21–5.27 (m, 3H) 5.9 (m, 1H)

A mixture of 102 mg of the N-allyloxycarbonyl derivative, 4.4 mg of tetrakis(triphenylphosphine)palladium, 4.4 mg of triphenylphosphine and 44.5 mg of 2-ethylhexanoic acid in 15 ml of anhydrous methylene chloride was stirred at 25° C. for 21 hours. Methylene chloride was added, the organic phase was washed with a 8% sodium bicarbonate aqueous solution, dried over anhydrous sodium sulphate and evaporated under vacuum. The residue was taken with aqueous hydrochloric acid (pH=3) and then extracted with methylene dichloride and the combined extracts were dried over anhydrous sodium sulphate and concentrated to a small volume. Hydrogen chloride and diethylether was added to give the title compound (I, R=H, $R_1$=H) (76 mg, yield 81%).

TLC on Kieselgel plates (Merck $F_{254}$) using the solvent system chloroform/methanol/water (65:30:10) $R_f$=0.48.

By proceeding analogously the following compounds can be prepared:

4-demethoxy-8-fluoro-3'deamino-4'-deoxy-4'-epi-aminodaunorubicin hydrochloride (I, R=H, $R_1$=H)

H-NMR of the corresponding allyloxycarboxyamido derivative is reported:

H-NMR (200 MHz, $CDCl_3$, inter alia δ): 3.19 (d, J=19 Hz, 1H, H-10 ax) 3.33 (dd, $J_{H-F}$=3.6 Hz, J=19 Hz, 1H, H-10 e); 4.91 (dd, $J_{H-F}$=50 Hz, 1H, H-8); 5.14 (dd, $J_{H-F}$=12 Hz, 1H, H-7); 5.18–5.27 (m, 3H, H-1'+—CH═$CH_2$)

8-Fluoro-3'-deamino-4'-deoxy-4'-epi-aminodaunorubicin hydrochloride (I, R=H, $R_1$=$OCH_3$)

H-NMR of the corresponding allyloxycarboxyamido derivative is reported:

H-NMR (200 MHz, $CDCl_3$, inter alia δ): 3.19 (d, J=19 Hz, 1H, H-10 ax); 3.48 (dd, $J_{H-F}$=3.6 Hz, J=19 Hz, 1H, H-10 e); 4.10 (s, 3H, $OCH_3$)

8-Fluoro-3'-deamino-4'-deoxy-4'aminodaunorubicin hydrochloride (I, R=H, $R_1$=$OCH_3$)

H-NMR of the corresponding allylcarboxyamido derivative is reported:

H-NMR (200 MHz, $CDCl_3$, inter alia δ): 3.17 8d, J=19 Hz, 1H, H-10 ax); 3.52 (dd, $J_{H-F}$=3.6, J==19 Hz, 1H, H-10 e); 4.08 (s, 3H, $OCH_3$)

EXAMPLE 17

4-demethoxy-8-fluoro-3'-deamino-4'-deoxy-4'-epi-aminodoxorubicin hydrochloride (I, R=OH, $R_1$=H)

According to the procedure described in U.S. Pat. No. 4,122,076 a solution of 100 mg of 4-demethoxy-8-fluoro-3'-deamino-4'-deoxy-4'-epi-aminodaunorubicin hydrochloride (IV, $R_1$=H, $R_2$=$NH_2$) prepared as described in EXAMPLE XVII in 2,5 ml of anhydrous methanol and 5 ml of dioxane was treated under stirring with a solution of 490 mg of bromine in 5 ml of methylene dichloride to afford the crude 14-bromo-4-demethoxy-8-fluoro-3'-deamino-4'-deoxy-4'-epi-daunorubicin which was precipitated by adding diethyl ether. The crude product was dissolved in a mixture of 5 ml of acetone and 1 ml of water and treated with 150 mg of sodium formate. The reaction mixture was stirred at room temperature for 36 hours, than water was added and extracted with methylene chloride. The aqueous phase was added with 3 ml of 8% aqueous solution of sodium hydrogen carbonate and extracted with methylene dichloride. The combined organic extracts were dried over anhydrous sodium sulphate, concentrated under vacuum to a small volume and treated with methanolic hydrogen chloride (pH=3.5) and diethyl ether to give the title compound (I, $R_1$=H, R=OH) (77 mg, yield 75%).

TLC on Kieselgel (Merck $F_{254}$) using the solvent system chloroform/methanol/water (65:30:10) $R_f$=0.31

By proceeding analogously starting from the corresponding daunorubicin derivatives (I, R=H, $R_1$=H or $OCH_3$) the following compounds can be prepared:

4-demethoxy-8-fluoro-3'-deamino-4'-deoxy-4'-aminodoxorubicin hydrochloride (I, R=OH, $R_1$=H)

TLC on Kieselgel (Merck $F_{254}$) using the solvent system chloroform/methanol/water (65:30:10) $R_f$=0.34

8-fluoro-3'-deamino-4'-deoxy-4'-aminodoxorubicin hydrochloride (I, R=OH, $R_1$=$OCH_3$)

TLC on Kieselgel (Merck $F_{254}$) using the solvent system chloroform/methanol/water (65:30:10) $R_f$=0.29

8-fluoro-3'-deamino-4'-deoxy-4'-epi-aminodoxorubicin hydrochloride (I, R=OH, $R_1$=$OCH_3$)

TLC on Kieselgel (Merck $F_{254}$) using the solvent system chloroform/methanol/water (65:30:10) $R_f$=0.27

To prepare a pharmaceutical composition suitable for therapeutic use, a suitable quantity of the active principle can for example be dissolved in bidistilled water for injectable use, to a concentration of 1–10 mg/ml. The solution obtained in this manner can then be lyophilized after adding a suitable carrier (such as mannitol or lactose) either with or without appropriate preservatives, and then divided into sterile vials ready for subsequent use.

We claim:

1. An 8-fluoroanthracyclineglycoside compound of the formula (I):

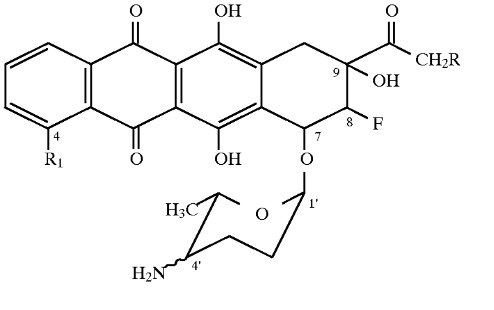

(I)

where:

R=H, OH, or OR";

$R_1$=H, OH, or $OCH_3$;

R"=CHO—$COCH_3$ or an acyl residue derived from a carboxylic acid containing up to 6 carbon atoms;

and $NH_2$ indicates that the amino substituent can be in the axial or equatorial configuration;

or a pharmaceutically acceptable salt thereof.

2. A compound as defined in claim 1 which is 4-demethoxy-8-fluoro-3'-deamino-4'-deoxy-4'-amino-daunorubicin or a hydrochloride salt thereof.

3. A compound as defined in claim 1 which is 4-demethoxy-8-fluoro-3'-deamino-4'-deoxy-4'-epi-aminodaunorubicin or a hydrochloride salt thereof.

4. A compound as defined in claim 1 which is 8-fluoro-3'-deamino-4'-deoxy-4'-aminodaunorubicin or a hydrochloride salt thereof.

5. A compound as defined in claim 1 which is 8-fluoro-3'-deamino-4'-deoxy-4'-epi-aminodaunorubicin or a hydrochloride salt thereof.

6. A compound as defined in claim 1 which is 4-demethoxy-8-fluoro-3'-deamino-4'-deoxy-4'-aminodoxorubicin or a hydrochloride salt thereof.

7. A compound as defined in claim 1 which is 4-demethoxy-8-fluoro-3'-deamino-4'-deoxy-4'-epi-aminodoxorubicin or a hydrochloride salt thereof.

8. A compound as defined in claim 1 which is 8-fluoro-3'-deamino-4'-deoxy-4'-aminodoxorubicin or a hydrochloride salt thereof.

9. A compound as defined in claim 1 which is 8-fluoro-3'-deamino-4'-deoxy-4'-epi-aminodoxorubicin or a hydrochloride salt thereof.

10. A compound as defined in claim 1 which is 8-fluoro-3'-deamino-4'-deoxy-4'-aminocarminomicin or a hydrochloride salt thereof.

11. A compound as defined in claim 1 which is 8-fluoro-3'-deamino-4'-deoxy-4'-amino-4'-epi-carminomicin or a hydrochloride salt thereof.

12. A pharmaceutical composition comprising a therapeutically effective amount of an anthracyclineglycoside of formula I in accordance with claim 1, or a pharmaceutically acceptable salt thereof, in mixture with a pharmaceutically acceptable diluent or carrier.

13. A method of treating a tumor, said method comprising administering to a host afflicted with a tumor an effective amount of an anti-tumor agent which comprises a compound of claim 1.

14. Therapeutic compositions with antitumor activity comprising as active principle a therapeutically effective amount of one or more compounds of formula (I) or their therapeutically acceptable salts as defined in claim 1 in mixture with inert diluents and excipients.

15. A method as defined in claim 13 wherein the tumor is a solid tumor.

16. A composition as defined in claim 12 which contains a sufficient amount of the compound of formula (I) to provide a dose of 1–300 $mg/m^2$.

* * * * *